United States Patent [19]

Butler et al.

[11] Patent Number: 4,894,476

[45] Date of Patent: Jan. 16, 1990

[54] GABAPENTIN MONOHYDRATE AND A PROCESS FOR PRODUCING THE SAME

[75] Inventors: Donald E. Butler, Holland; Barbara J. Greenman, Door, both of Mich.

[73] Assignee: Warner-Lambert Company, Morris Plains, N.J.

[21] Appl. No.: 188,819

[22] Filed: May 2, 1988

[51] Int. Cl.$^4$ ........................................... C07C 101/14
[52] U.S. Cl. .................................................. 562/504
[58] Field of Search ................ 560/122, 125; 562/504, 562/507

[56] References Cited

U.S. PATENT DOCUMENTS 4,024,175  5/1977  Satzinger ..................... 260/468 J
4,087,544  5/1978  Satzinger ..................... 424/303

Primary Examiner—Michael L. Shippen
Attorney, Agent, or Firm—Elizabeth M. Anderson

[57] ABSTRACT

A novel crystalline form of gabapentin and a novel processes for the small and large scale preparations of the anticonvulsant compound in a highly pure state is disclosed. This novel hydrate is produced by a cost effective process which provides an additional purification stage.

2 Claims, No Drawings

GABAPENTIN MONOHYDRATE AND A PROCESS FOR PRODUCING THE SAME

BACKGROUND OF THE INVENTION

Gabapentin is a generic term used to identify the chemical compound (1-aminomethyl)-1-cyclohexaneacetic acid.

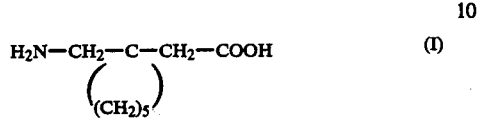
(I)

It is useful in therapy of certain cerebral disorders such as certain forms of epilepsy, faintness attacks, hypokinesia and cranial traumas. U.S. Pat. Nos. 4,024,175 and 4,087,544 cover the compound and its uses. They also disclose an acid salt, i.e. gabapentin.hydrochloride hydrate in a ratio of 4:4:1 and a sodium salt of gabapentin hydrate in a ratio of 2:1. These patents are hereby incorporated by reference.

The patents describe various processes for the preparation of this and similar compounds of general formula

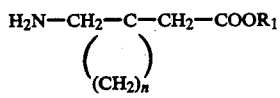

wherein $R_1$ is a hydrogen atom or a lower alkyl radical and n is 4, 5, or 6 and the pharmaceutically acceptable salts thereof, which depend upon known methods used for the preparation of primary amines or amino acids.

All examples of the syntheses end in an isocyanate or urethane that can easily be converted into the desired (1-aminomethyl)-1-cyclohexaneacetic acid by acidic hydrolysis (preferred) to give an acid or basic hydrolysis to give a basic salt or followed by acidification to give an acid salt.

SUMMARY OF THE INVENTION

The present invention provides crystalline gabapentin monohydrate, a novel, highly pure substance of reasonable bulk density suitable for formulation in the desired forms such as capsules or tablets. Its properties are those sought in a pharmaceutical product. The present invention provides both a small scale and a large scale method for producing gabapentin monohydrate. This form, the hydrate of the free amino acid, has the advantage of being less expensive to produce than the known form of gabapentin. The process has the advantage of having barely detectable residues of solvents such as 2-propanol. No detectable methanol or ethanol residuals remain. Also, the process for producing the hydrate provides an extra purification step even if one goes on to produce the anhydrous material. The hydrate saves 12–13% of the total yield of gabapentin by eliminating the losses confronted in the final recrystallization. The hydrate also saves the cost of solvents, man hours, and utilities used in the final recrystallization. The product is a very pretty crystal which is stable at ambient temperatures (20°–25° C.).

DETAILED DESCRIPTION

The instant invention is a novel form of gabapentin, crystalline gabapentin monohydrate with the following unique X-ray diffraction properties.

| Spacing 'd' | Relative Intensities |
| --- | --- |
| 14.255 | 99 |
| 7.196 | 99 |
| 5.438 | 4 |
| 4.848 | 99 |
| 4.575 | 7 |
| 4.291 | 7 |
| 3.633 | 99 |
| 3.376 | 21 |
| 3.220 | 9 |
| 2.903 | 28 |
| 2.771 | 23 |
| 2.356 | 7 |
| 2.344 | 12 |

Crystalline gabapentin monohydrate has a density within the range of 0.35 to 0.9 g/cm³. The observed is 0.35 to 0.49 g/cm³ + or −0.02. The crystals are obtained in a highly pure state. They are of a reasonable bulk density. The term reasonable means having a density above 0.4 g/cm³. These characteristics readily lend themselves to pharmaceutical formulating operations.

The present invention also provides a process for producing gabapentin monohydrate on a small scale. This process is for the preparation of a compound of formula

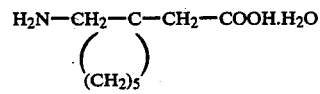
II which comprises:
(a) pouring a 1N solution of an acid salt of (1-aminomethyl)-cyclohexaneacetic acid onto an ion exchange column in the basic form and eluting that column with deionized water;
(b) collecting and testing fractions from step (a) for ion and product;
(c) concentrating the fractions containing product from step (b) to a slurry;
(d) mixing the slurry from step (c) with alcohol to produce a suspension and after cooling;
(e) filtering off the desired product, washing it with cold alcohol and drying it in vacuo.

Useful acid salts are hydrobromide, sulphate, methane sulfonate, hydrochloride and the like. The preferred acid salt in step (a) is the hydrochloride.

Preferably in step (b) the chloride ion is tested for by using a silver nitrate solution, but other analytical methods for chloride can be used by one skilled in the art. The product is tested by thin layer chromatography.

Preferably in step (c) the fractions are concentrated on a rotovap with about 29–31 inches vacuum at a temperature of from about 25° to about 50° C. to a volume of about three times the theoretical volume yield of 1:1 hydrate.

Preferably in step (d) the alcohol is 2-propanol and the suspension is cooled for from about 8 to about 20 hours.

The present invention further provides a process for the large scale production of gabapentin hydrate (1:1) which comprises:

A process for the preparation of a compound of formula

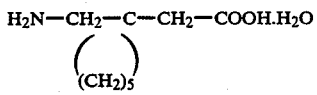

which comprises:
(a) pouring a solution of an acid salt of (1-aminomethyl)-cyclohexaneacetic acid in deionized water onto an ion exchange column in the basic form and eluting the column with deionized water;
(b) concentrating the eluate producing a slurry;
(c) cooling and adding alcohol to the slurry from step (b);
(d) cooling and centrifuging the slurry from step (c); and
(e) drying the precipitate of the desired product.

Useful acid salts include but are not limited to hydrobromide, sulphate, methanesulfonate, hydrochloride and the like. The preferred salt is the hydrochloride and in a preferred ratio is 4:4:1.

The preferred acid salt of (1-aminomethyl)-cyclohexaneacetic acid is the monohydrochloride hydrate in a ratio of 4:4:1.

Preferred process conditions in step (b) the eluate is concentrated in a glass-lined still at about 29-31 inches of vacuum at a temperature of from about 25° C. to about 50° C. to produce a slurry.

Preferred process conditions in step (c) the slurry is cooled to about 25° to about 45° C. for about 1 to 3 hours and the alcohol added is 2-propanol.

Preferred process conditions for step (d) include the slurry is cooled to about −10° C. to about 0° C. for about 12 to 16 hours.

Preferred process conditions for step (e) include the precipitate is dried in vacuo at about 25°-35° C. for about 8 to 24 hours.

The gabapentin monohydrate provides an extra purification step and can be used to produce the anhydrous material claimed in the United States Patents incorporated by reference.

The present invention further provides a process for the large scale production of essentially anhydrous gabapentin of the same crystal structure produced by the methods cited in the United States Patents incorporated by reference. This process for the preparation of the compound of formula

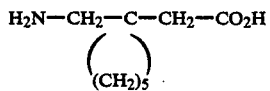

comprises:
(a) dissolving pure gabapentin monohydrate in methanol at 50° C. to 60° C.;
(b) diluting with 2-propanol and cooling to 0° C. to −10° C. the solution from step (a) resulting in a slurry;
(c) centrifuging the slurry from step (b) and drying the precipitate of gabapentin.

Preferred process conditions in step (a) the gabapentin monohydrate is dissolved in methanol in a ratio of 0.141 Kg of gabapentin monohydrate to 1.00 Kg of anhydrous methanol in a temperature range of about 50° C. to about 60° C.

Preferred process conditions in step (b) the solution is diluted with anhydrous 2-propanol in the ratio of 1 Kg of anhydrous 2-propanol to 1 Kg anhydrous methanol and the solution is chilled to 20° C. to 25° C. for two hours and then to −8° C. to −10° C. for sixteen to twenty hours.

Preferred process conditions in step (c) include the gabapentin is dried in vacuo at about 25° C. to 45° C. for about eight to forty-eight hours.

Since the compound of formula (II) has only extremely low toxicity, it can be administered enterally or parenterally within wide dosage ranges in liquid or solid form. As injection solution, water is preferably employed which contains the usual additives for injection solutions, such as stabilising agents, solubilising agents and/or buffers.

Additives of this kind include, for example, tartrate and citrate buffers, ethanol, complex-forming agents (such as ethylenediamine-tetraacetic acid and the non-toxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agaragar, calcium phosphate, magnesium stearate, animal and vegetable fats and solid high molecular weight polymers (such as polyethylene glycol); compositions suitable for oral administration can, if desired, also contain flavoring and/or sweetening agents.

The individual dosage for the compounds according to the present invention can be from 100 to 3000 mg/day for an adult, preferably from 600 to 2400 mg/day, and most preferably the dosage is about 1200 mg/day or as deemed necessary by a skilled physician.

Thus, the present invention also provides pharmaceutical compositions of the compound in admixture with a solid or liquid pharmaceutical diluent or carrier.

The preparation of gabapentin monohydrate is illustrated by the following nonlimiting examples.

EXAMPLE 1

Small Scale isolation of Gabapentin hydrate (1:1) ((1-aminomethyl)-cyclohexaneaceticacid.H$_2$O)

An ion exchange column is prepared by filling a glass column with 380 mL of Amberlite$^R$ IRA-68. The resin is rinsed with a dilute ammonia solution, 140 mL ammonium hydroxide in 3 L water, followed by deionized water to a neutral pH, (about 2 L). A 1 N solution of (1-aminomethyl)-cyclohexaneacetic acid hydrochloride is prepared by dissolving 64.6 g of (1-aminomethyl)-cyclohexaneacetic acid hydrochloride hydrate (4:4:1) in 310 mL of deionized water. This solution is filtered through a filter to remove any insoluble material or extracted with an organic solvent such as dichloromethane.

The solution is poured onto the column and drained to the top level of the resin. The column is eluted using deionized water at approximately 15 mL/min. Fractions of about 200–250 mL are collected. The first four fractions, about 1 L total, contain all of the product (TLC). Chloride is tested for using a silver nitrate solution. No chloride is usually detected in any of the fractions collected.

The first four fractions are concentrated on a rotovap with about 29–31 inches vacuum and the temperature <40° C. to a slurry, about 150 mL. This is mixed with 288 mL 2-proponal and the suspension is cooled in a refrigerator overnight. The white crystalline (1-aminomethyl)-cyclohexaneacetic acid hydrate (1:1) is filtered off, washed with cold 2-propanol, and dried in vacuo to yield 42.93 g.

Analytical data: HPLC: 89.27% w/w against dry analytical standard, $H_2O$: 9.68%±0.5, mp 156°–156.7° C. (dec), $CL^-$: 8.6 ppm.

Since this is a hydrate and does melt with decomposition, the melting point range can start as low as 154° C. and can end as high as 162° C.

EXAMPLE 2

Large Scale isolation of Gabapentin hydrate (1:1) ((1-aminomethyl)-cyclohexaneacetic acid hydrate (1:1))

An ion exchange column (60 inch bed height, 15 inch radius) is charged with 250 L of filtered deionized water followed by 700 L (504 Kg wet) Amberlite$^R$ IRA-68 resin. The resin is backwashed with 2000 L of filtered deionized water. The resin is treated with 3700 L of filtered deionized water that has been mixed with 60.6 Kg of concentrated hydrochloric acid. The acid treatment is repeated with fresh acid. The resin is washed with 6400 L of filtered deionized water. The resin is treated with 1770 L of a 4% solution of sodium hydroxide. The resin is washed with 3200 L of deionized water.

The resin is treated with 3700 L of filtered deionized water that has been mixed with 60.6 Kg of concentrated hydrochloric acid. The acid treatment is repeated with fresh acid. The resin is washed with 6400 L of filtered deionized water. The resin is treated with 1770 L of a 4% solution of sodium hydroxide. The resin is washed with 3200 L of deionized water.

The resin is treated with 3700 L of filtered deionized water that has been mixed with 60.6 Kg of concentrated hydrochloric acid. The acid treatment is repeated with fresh acid. The resin is washed with 6400 L of filtered deionized water. The resin is treated with a solution of 105 Kg of 28% ammonium hydroxide in 1700 L of deionized water. The resin is washed with 6400 L of deionized water.

A solution of 122 Kg (57.5 moles) of 1-(aminomethyl)-cyclohexaneacetic acid monohydrochloride hydrate (4:4:1) in 472 Kg of deionized water is filtered to remove any insoluble material or extracted with an organic solvent such as dichloromethane and then is applied to the top of the ion exchange column and eluted with 3750 Kg of deionized water. The presence of chloride ion is tested for using silver nitrate solution and the product is tested for by using thin layer chromatography. The eluate is concentrated in a 500 gallon glass-lined still at about 29–31 inches of vacuum and wall temperature of <50° C. A total of 3500 Kg of water is removed. The resulting slurry is cooled to about 18°–20° C. and 248.5 Kg of 2-propanol is added. The slurry is cooled at −12°–−8° C. for 16 hours, centrifuged and washed with 2-propanol. The precipitate is dried in vacuo about 29–31 inches at 25°–30° C. to yield 86 Kg of 1-(aminomethyl)-cyclohexaneacetic acid hydrate (1:1).

Analytical data: HPLC: 89.4 w/w against dry reference standard, $H_2O$ (Karl Fischer): 9.69%±0.5, mp 156°–156.7° C. (dec), $CL^-$: 30 ppm.

Since this is a hydrate and does melt with decomposition, the melting point range can start as low as 154° C. and can end as high as 162° C.

EXAMPLE 3

Large Scale Isolation of anhydrous 1-(aminomethyl)-cyclohexaneacetic acid from gabapentin monohydrate ((1-aminomethyl)-cyclohexaneacetic acid hydrate (1:1))

A slurry of 179 Kg of 1-(aminomethyl)-cyclohexaneacetic acid monohydrate and 1266 Kg of anhydrous methanol is heated to 60° C. to give a complete solution. The solution is diluted with 1266 Kg of anhydrous 2-propanol and the solution is cooled to 20° C. to 25° C. for two hours and then is cooled to −8° C. to −10° C. for twenty hours. The resulting slurry is centrifuged and the precipitate is dried in vacuo at 35° C. for forty-eight hours to yield 145 Kg of white, crystalline 1-(aminomethyl)-cyclohexaneacetic acid.

Analytical data: HPLC: 100.6% w/w against dry analytical standard, $H_2O$: 0.09%. $CH_3OH$: 0.01%, $(CH_3)_2CHOH$: 0.01%, $CL^-$: 22 ppm, Melting point: 161.7°–162.6° C. (dec.).

We claim:

1.

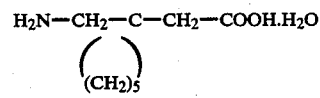

exhibiting essentially the following X-ray diffraction data:

| Spacing 'd' | Relative Intensities |
| --- | --- |
| 14.255 | 99 |
| 7.196 | 99 |
| 5.438 | 4 |
| 4.848 | 99 |
| 4.575 | 7 |
| 4.291 | 7 |
| 3.633 | 99 |
| 3.376 | 21 |
| 3.220 | 9 |
| 2.903 | 28 |
| 2.771 | 23 |
| 2.356 | 7 |
| 2.344 | 12 |

2.

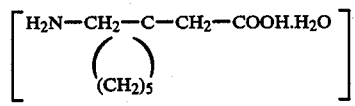

according to claim 1 having a bulk density within the range of 0.35 to 0.49 g/cm$^3$.

* * * * *